United States Patent
Hunger et al.

(10) Patent No.: US 9,551,641 B2
(45) Date of Patent: Jan. 24, 2017

(54) DRILLING MEASURING DEVICE, EXCHANGEABLE NEEDLE CARTRIDGE, EXCHANGEABLE DOCKING DEVICE, AND EXCHANGEABLE TOOL

(75) Inventors: Erich Hunger, Karlsruhe (DE); Sebastian Hunger, Leimen (DE)

(73) Assignee: IML-INSTRUMENTA MECHANIK LABOR GMBH, Wiesloch (DE)

( * ) Notice: Subject to any disclaimer, the term of this patent is extended or adjusted under 35 U.S.C. 154(b) by 495 days.

(21) Appl. No.: 14/124,758

(22) PCT Filed: Jun. 8, 2012

(86) PCT No.: PCT/DE2012/000607
§ 371 (c)(1),
(2), (4) Date: Dec. 9, 2013

(87) PCT Pub. No.: WO2012/167777
PCT Pub. Date: Dec. 13, 2012

(65) Prior Publication Data
US 2014/0109660 A1    Apr. 24, 2014

(30) Foreign Application Priority Data
Jun. 8, 2011   (DE) .................. 10 2011 103 636

(51) Int. Cl.
*B23B 41/00* (2006.01)
*G01N 3/40* (2006.01)
(Continued)

(52) U.S. Cl.
CPC ................ *G01N 3/40* (2013.01); *B23B 41/00* (2013.01); *B27C 3/08* (2013.01); *G01N 33/0098* (2013.01); *G01N 33/46* (2013.01); *Y10T 408/564* (2015.01)

(58) Field of Classification Search
CPC ....... B27C 3/08; G01N 33/0098; G01N 33/46; G01N 3/40; Y10T 408/564
(Continued)

(56) References Cited

U.S. PATENT DOCUMENTS 3,750,343 A    8/1973   Johnson
4,279,552 A *  7/1981   Epstein ................ B25H 1/0078
                                                          408/112

(Continued)

FOREIGN PATENT DOCUMENTS

DE          91 01 397 U1    4/1991
DE          41 22 494 A     3/1992

(Continued)

OTHER PUBLICATIONS

International Search Report, PCT/DE2012/000607, Sep. 26, 2012, 3 pgs.

*Primary Examiner* — Hezron E Williams
*Assistant Examiner* — Gedeon M Kidanu
(74) *Attorney, Agent, or Firm* — Paul D. Strain, Esq.; Strain & Strain PLLC (57) ABSTRACT

Disclosed herein is an exchangeable needle cartridge for a drilling measuring device with a guiding device for a drilling needle. The guiding device includes a telescopic tube with a plurality of telescopic tube sections which extends between a working end, at which a retainer for retaining the drilling needle in a rotationally fixed manner is arranged, and a docking end, at which a docking device for coupling the telescopic tube to a driving device of the drilling measuring device is arranged. Also disclosed is a docking device comprising a coupling device for transmitting torque from the driving device of the drilling resistance measuring device to the telescopic tube, a transmission device for converting the rotational motion of the driving device of the drilling measuring device into a linear motion of the tele- (Continued)

scopic tube, and furthermore structure for detachably fastening the exchangeable needle cartridge to the drilling measuring device.

23 Claims, 7 Drawing Sheets

(51) Int. Cl.
*G01N 33/00* (2006.01)
*G01N 33/46* (2006.01)
*B27C 3/08* (2006.01)

(58) Field of Classification Search
USPC .............................................. 408/110; 73/82
See application file for complete search history.

(56) References Cited

U.S. PATENT DOCUMENTS

| | | | | |
|---|---|---|---|---|
| 4,671,105 A * | 6/1987 | Kamm | ..................... | G01N 3/42 73/81 |
| 6,290,437 B1 * | 9/2001 | Mattheck | ................. | B25F 3/00 408/11 |
| 6,484,820 B1 * | 11/2002 | Tibussek | ................... | E21B 4/02 166/355 |
| 7,404,696 B2 * | 7/2008 | Campbell | ............... | B25F 5/021 362/119 |
| 7,617,884 B2 * | 11/2009 | Rubie | ..................... | E21B 7/025 173/11 |
| 8,308,732 B2 * | 11/2012 | Millett | ............... | A61B 17/1728 606/96 |
| 8,720,603 B2 * | 5/2014 | Bauer | ..................... | E21B 7/124 166/358 |

FOREIGN PATENT DOCUMENTS

| | | | | |
|---|---|---|---|---|
| DE | 4122494 A1 * | 3/1992 | ............... | G01N 3/42 |
| DE | 91 17 283 U1 | 8/1999 | | |
| DE | 10 031 395 A1 | 4/2001 | | |
| DE | 41 22 494 B4 | 3/2004 | | |
| DE | 10 2005 013 752 A1 | 10/2006 | | |
| EP | 09 77 653 B1 | 6/2003 | | |
| FR | 2 760 842 A1 | 9/1998 | | |
| WO | WO 98/47671 A1 | 10/1998 | | |

* cited by examiner

DRILLING MEASURING DEVICE, EXCHANGEABLE NEEDLE CARTRIDGE, EXCHANGEABLE DOCKING DEVICE, AND EXCHANGEABLE TOOL

CROSS-REFERENCE TO RELATED PATENT APPLICATIONS

This application is a National Stage of International Application No. PCT/DE2012/000607, filed Jun. 8, 2012, which is based upon and claims the benefit of priority from prior German Patent Application No. 10 2011 103 636.2, filed Jun. 8, 2011, the entire contents of all of which are incorporated herein by reference in their entirety.

The following invention relates to exchangeable needle cartridges for drilling measuring devices and to drilling measuring devices themselves, as well as to an exchangeable docking or coupling device and to an exchangeable tool by way of which the exchangeable docking device is able to be mounted and removed.

All the objects can be utilized as a kit, the devices as claimed in the invention making it possible in each case, in the event of components which are connected to the most applicable part, namely the needle, becoming defective, for the drilling measuring device to be made fit for use again on site and as rapidly as possible.

Drilling resistance measuring devices, for example, are known from the prior art for testing trees and timber components in order to test them as regards their structure and defects, for instance rottenness. A drilling resistance measuring device for determining the inner state of trees or objects made of timber is described for instance in EP 09 77 653: It is essentially similar to a hand drill and has means for registering the torque of the supported drilling needle. The drill attachment is connected to the drive unit to form a device unit so that the overall length of the drilling resistance measuring device does not exceed the length of the drill attachment or only exceeds it a little.

A device for carrying out drilling resistance measurements is also known from DE 10 031 393 A1 in which the drilling tool drive is allowed to move into a cup telescope in order to provide improved guidance for the drill.

If, in the case of known drilling measuring devices, a needle is damaged during drilling, a complex and arduous removal procedure of the old needle is necessary to exchange the long needle which is supported by means of different devices, followed by the installation of the new needle.

Proceeding from said prior art, the object is to create a device to make it easier to exchange the needle for drilling measuring devices.

Said object is achieved by the exchangeable needle cartridge with the features of claim 1.

It is also possible for the needle to break off in its "drill chuck" such that it becomes necessary to replace said needle for this or also for any other reason. The object of providing an exchangeable needle cartridge with an exchangeable drill chuck, or more precisely with a device which replaces a classic drill chuck, is achieved by the exchangeable needle cartridge with the exchangeable docking device as claimed in claim 2 and as claimed in claim 14.

Additionally disclosed is an improved drilling measuring device with the features of claim 16, said drilling measuring device making it possible to replace a defective needle or even a docking device for the needle on the drilling device rapidly and at little mounting expenditure.

An exchangeable tool with the features of claim 19 enables the docking device for the needle on the drilling device to be exchanged in a simple manner.

Further developments of the devices are provided in the respective sub-claims.

An exchangeable needle cartridge as claimed in the invention for a drilling measuring device includes a telescopic tube with a number of telescopic tube portions which form a guiding device for a drilling needle. The tube portions which form the telescope extend from an operating end of the telescope up to its docking end: The "operating end" of the telescopic tube is to be understood as the end on which there is a mounting, by means of which the drilling needle is held in a non-rotatable manner. The operating end of the telescopic tube is therefore designed to carry out a measuring operation on the object to be tested. The "docking end", in contrast, is to be understood as the end of the telescopic tube which docks on a drive or is coupled with a drive, by means of which the drilling needle is made to rotate. In order to couple the telescopic tube with a driving device of a drilling measuring device, the exchangeable needle cartridge has a docking device on which the docking end of the telescopic tube is arranged. Said docking device has a coupling device in order to transmit the torque from the driving device of the drilling measuring device to the telescopic tube, and in addition it has a gear device in order to convert the rotational movement of the driving device of the drilling measuring device into a linear movement of the telescopic tube, and additionally has means by way of which the exchangeable needle cartridge is able to be releasably fastened on the drilling measuring device.

Thus, as a result of the exchangeable needle cartridge as claimed in the invention, it is possible for the needle, together with the components guiding and moving it, to be able to be exchanged in toto from the interface to the drive if a defect occurs.

The design of the device is kept advantageously simple.

In addition, the docking device can be developed advantageously so as to be exchangeable: It then forms quasi an "exchangeable docking device" which has a drill chuck portion with a magnetic mounting for the docking end of the telescopic tube and a receiving portion which holds the drill chuck portion so as to be releasable and is connectable to the drilling measuring device.

The receiving portion can remain permanently on the housing which surrounds the drive for the drilling needle. According to popular understanding, a "drilling machine" is formed by a housing, a drive and a receiving device, a "drilling machine" of this type only being usable as a drilling measuring device with the needle.

The "drill chuck portion" which has a coupling function is releasably connectable at one end to the telescopic tube and at the other end to the receiving portion. Whilst the receiving portion has at least one fastening device, by means of which the receiving portion is fastened on the drilling measuring device or the housing for the drive such that it is also able to remain there permanently, if desired, the drill chuck portion is releasably connectable at one end to the telescopic tube and at the other end to the receiving portion. Consequently, it is possible to exchange said drill chuck portion, in which, for instance, a piece of a broken-off needle is able to remain, without any effort or expenditure.

For this purpose it is proposed as claimed in the invention that the drill chuck portion of the exchangeable docking device can be screw-connected to the receiving portion by means of a screw mechanism. Different suitable threaded forms are known to the expert for this purpose.

In order to simplify the exchange of the exchangeable docking device, that is the removal and mounting of the exchangeable docking device, on an end face of its end pointing away from the receiving portion, the drill chuck portion has engagement means which are realized for the purpose of being moved into engagement with complementary engagement means of an exchangeable tool for the exchangeable docking device.

During removal/mounting of the exchangeable docking device, the exchangeable tool is consequently simply placed onto the drill chuck portion of the exchangeable docking device so that it engages and the screw connection is released/tightened.

The engagement means present on the drill chuck portion can be bores, at least two bores, located opposite one another, having to be provided in order to enable transmission of the torque from the exchangeable tool to the exchangeable docking device. Said bores can be arranged on a bore circle offset by approximately 180°. Three or bores are better since in this way the force to be transmitted per bore is reduced. Dowel pins which can be inserted into the bores so that the torque is able to be transmitted are then to be provided at a corresponding point on the exchangeable tool. Naturally, the engagement means can also have more complicated geometries—with reference to their cross sectional form, they can for instance be four-edged or multiple-edged or oval.

In a further embodiment of the invention, the docking device of the telescopic tube includes a magnetic mounting which is releasably connected to the docking end of the telescopic tube. In this case, it is insignificant whether the docking device is developed as the exchangeable docking device or as another, fixed docking device.

By means of the magnetic mounting, the docking end of the telescopic tube can be guided and mounted in an axially centered manner in the docking device in order to facilitate coupling the telescopic tube to the driving device and to support it in the coupled state. The coupling device for transmission of torque onto the telescopic tube can preferably be a simple claw coupling—but a latching coupling or a bayonet closure are also conceivable for the torque-transmitting coupling of the telescopic tube and the driving device. The magnetic mounting ensures that there are no time-consuming or complicated mounting steps to be performed at the docking end when the exchangeable needle cartridge is exchanged since the necessary holding force is generated on the docking end as a result of the magnetic force, which can be up to 12 kg.

In a suitable embodiment, the magnetic mounting is consequently in the form of a hollow cylinder and the docking end of the telescopic tube can be received in the bore of the hollow cylinder. In this case, a centering disc, which when docked on the docking device, or on the magnetic mounting included by the docking device, can abut against the docking end of the telescopic tube, can be provided on the docking end of the telescopic tube. This is possible in particular when, in an advantageous embodiment, a tube portion with the smallest outer diameter is present on the docking end such that the tube diameter increases in the direction of the distal end of the exchangeable needle cartridge, proceeding from an arrangement with a drive. In principle, however, it is also possible to select a reverse arrangement, or to use a telescopic device which in each case has several sequences, each sequence consisting of several tube portions which are arranged in a telescopic manner with reference to one another.

On the operating end of the telescopic tube, in contrast, there is a mounting for the drilling needle which has a corresponding receiving opening and which can be realized in a suitable manner as a threaded ring in order to be screw-connected to the tube portion end of the telescopic tube on the operating side. Thus, if the exchangeable needle cartridge has to be exchanged during an operation, the cartridge with a defective needle can be put to one side in order to exchange the needle easily at a suitable moment by removing it from the telescopic tube as a result of unscrewing the threaded ring. In an advantageous manner, the measuring work at the object only has to be interrupted very briefly to exchange the needle.

In an advantageous manner, the exchangeable needle cartridge can include a rail along which is arranged the docking device, which in the end is connected to the telescopic tube in the described manner. The rail has fastening means, in particular engagement means, which can be realized, for instance, as a bifurcation in order to connect the rail releasably to the drilling measuring device when the exchangeable needle cartridge is to be moved into an arrangement for use and is consequently to be connected to the drive. As a result of the development as a bifurcation, it is possible in a simple manner to connect the cartridge to the bore measuring device which has a housing which has a corresponding recess in order to receive said bifurcation. Obviously other pairs of fastening means are conceivable.

In one embodiment, the operating end of the telescope is received in a guiding housing when it is in the extended state. The guiding housing is also fastened along the rail on the end which is remote from the docking device and stabilizes the arrangement when the overall unit of needle and telescope is present in its maximum length. The guiding housing can also have guiding means in order to guide the drilling needle of the telescopic tube when the telescopic tube extends until the operating end the guiding housing is reached.

In yet another embodiment of the invention, the rail can form one side of an exchangeable needle cartridge housing which can simply be inserted or placed into a higher-ranking housing which is associated with the drilling measuring device. In an advantageous manner, the geometry and the length of the drilling measuring device housing can be developed such that the exchangeable needle cartridge housing or the embodiment with the rail can be received therein such that the needle is protected securely therein when the drilling measuring device is not operating. In a particularly suitable manner, the exchangeable needle cartridge closes off flush with the open edge of the drilling measuring device housing, for instance by means of the cover of the guiding housing.

Thus, in an advantageous manner, by releasing the engagement means by means of a handle, the housing of the exchangeable needle cartridge can be removed out of the housing of the drilling measuring device and the cartridge can be removed. A new exchangeable needle cartridge is inserted and in this way a defective needle can be exchanged with the smallest possible amount of time expended and without carrying out complicated removal operations.

In addition, in a further embodiment of the exchangeable needle cartridge as claimed in the invention, said exchangeable needle cartridge has at least one bearing for the telescopic tube, said bearing being arranged on a tube portion which is located between the operating end and the docking end. The bearing or bearings is/are displaceable with the tube portion along the rail or in the housing such that the bearing is moved with the corresponding tube portion when the telescopic tube is telescoped, that is when it is transferred into the expanded position.

It can be advantageous to use several bearings depending on the length of the telescopic tube and on the number of tube portions used.

In a particularly advantageous manner, the exchangeable needle cartridge can include a gear device with a spindle drive which is connected to the operating end of the telescopic tube in order to ensure simple and secure telescoping with a certain drive for the drilling needle.

In principle, the exchangeable docking device, which can be a component of the exchangeable needle cartridge, can also serve just as well for the telescopic tube needle guiding device which is realized as claimed in the invention as for the docking or coupling of other guiding devices for a drilling needle which are to be operated with a drilling measuring device. The embodiment of the guiding device in which said guiding device is realized as a telescopic tube with several telescopic tube portions is particularly suitable for the measuring operation described here.

As shown above, the exchangeable docking device has a drill chuck portion with a magnetic mounting and a receiving portion which is connectable to the drilling measuring device. In this case, the drill chuck portion is releasably connectable at one end to the guiding device and at the other end to the receiving portion and the receiving portion has at least one fastening device which is realized for the purpose of fastening the receiving portion on the drilling measuring device.

In this application too, the drill chuck portion is connectable to the receiving portion by means of a rotatable mechanism, and on an end face of its end pointing away from the receiving portion, the drill chuck portion has engagement means, such as, for instance, the named two or more bores which can be moved into operative engagement with complementary engagement means of an exchangeable tool.

In addition, disclosed in the present case is a drilling measuring device for testing material quality, said drilling measuring device including a driving device for driving a drilling needle. The drilling measuring device as claimed in the invention has a housing in which the drilling needle is arranged on an exchangeable needle cartridge as claimed in the present invention. Thus, the drilling needle is docked with the driving device of the drilling measuring device by means of the telescopic tube and the docking device of the exchangeable needle cartridge and is driven in the state of use by the rotating telescopic tube being extended.

Such a drilling measuring device can be a drilling resistance measuring device or a moving force measuring device which also operates according to the principle of operation of a drilling machine.

In addition, an exchangeable tool is disclosed which serves to exchange, or rather to mount or remove an exchangeable docking device, as is present either as a component of the exchangeable needle cartridge of the present invention, or which can also be an exchangeable docking device which is not present in a cartridge.

The exchangeable tool has a central portion, the one end of which is realized as an engagement end for engagement with the exchangeable docking device, and which has on the end face a cylindrical pin which is arranged in a center-axial manner. Said pin has an outer circumference which corresponds to an inner circumference of the bore of the hollow cylinder of the exchangeable docking device. On the end face of said central portion there are at least two engagement means which are realized for engagement with the complementary engagement means which are arranged on the end face of the drill chuck portion of the exchangeable docking device. The other end of the central portion is realized as an actuating end and extends into a handle.

The handle is to be realized such that the torque necessary to release the exchangeable docking device can be generated in an ergonomical manner with as little manual force as possible.

The engagement means on the tool can be dowel pins, and the complementary engagement means, which are present on the end face of the drill chuck portion of the exchangeable docking device, are bores which correspond in form and diameter to the dowel pins. This can also be reversed such that the dowel pins are present on the drill chuck portion, the complementary bores in this respect having to be arranged in the exchangeable tool. In addition, other complementary pairs of engagement means are also conceivable.

The center-axially arranged cylindrical shaft portion of the exchangeable tool can be present either as a short portion only on the engagement end (with the drill chuck portion) of the central portion as a positioning aid. The handle is then formed by a different component or is incorporated thereby. Or it can extend center-axially through the entire central portion and project out of said portion at the actuating end. The shaft portion, on its free end, can then have a radial bore through which a bar protrudes and forms the handle.

It is also possible for the center-axially arranged cylindrical shaft portion to be hollow and to receive an inner shaft, which then extends center-axially through the central portion and projects out of said portion at the actuating end in the previously shown manner, and has on its free end the radial bore with the through-bar and forms the handle.

In principle, the handle can also have a different form or can be realized in a different manner.

In an advantageous manner, the center-axially arranged cylindrical shaft portion is held on the end face of the engagement end of the central portion by a bearing cylinder which is arranged in the central portion such that a centering projection is realized which, in the case of an arrangement of the exchangeable tool in the exchangeable needle cartridge for mounting/removal is guidable in a precisely fitting manner over the step which is formed on the docking device as a result of a recess being provided for the centering disc.

If the exchangeable docking device is part of an exchangeable needle cartridge, the outer circumference of the central portion should be smaller than or equal to a circumference of an opening which is present in the cartridge cover. The drilling needle, which is held at its operating portion by a mounting which forms the "end" of the telescopic portion, usually extends out of said opening on the cartridge cover.

The opening, in one embodiment, can be matched precisely to a mounting which is realized as a threaded ring for screw-connection onto the operating end of the telescopic tube and which has a drilling needle receiving means which closes off exactly with the opening and can be placed or put thereon.

The exchange of the needle can then be effected by the threaded ring and the drilling needle receiving means being released and the needle being pulled out using tongs or something else. In this case, the housing, which surrounds the guiding device for the drilling needle which is realized as a telescopic tube with several telescopic tube portions, remains fastened on the drilling measuring device, or rather on or in the housing which surrounds the drive. It is simply necessary to release the needle from the drilling needle receiving means on the cover of the exchangeable needle cartridge since the magnetic fastening of the needle on the coupling can be overcome by pulling.

The same applies if the telescopic tube per se is to be removed. Here too, it is simply necessary to release the mounting on the cartridge cover; if it is the threaded ring included here, this is easily possible without expenditure on tools. Naturally, tongs can be used as an aid if the threaded ring which forms the mounting gets stuck.

If the docking device is then to be exchanged, in an advantageously simple and convenient manner the method of operation can be as follows without the housing which surrounds the telescopic tube having to be removed. To this end, as shown above, the needle is initially taken out of the guiding device; the telescopic tube, once the mounting or the threaded ring has been unscrewed, is then simply pulled out of the surrounding housing. In this case, it is advantageous for the guiding devices, which are provided on the telescopic tube to guide it along the rail, to be present on the smaller diameter tube portions and to be able to be developed such that they fit easily through the opening on the cartridge cover. The telescopic tube is pulled out, as an option is telescoped and put to one side, and the exchangeable tool is then put to use. The engagement end of the exchangeable tool is pushed in front through the opening in the cartridge cover until the provided engagement means, for instance the dowel pins, engage with the correspondingly complementary engagement means on the drill chuck portion. As the geometries of the engagement means and their arrangements are matched to one another and the outer diameter of the central portion of the exchangeable tool corresponds to the opening diameter of the cartridge cover opening, the exchangeable tool can be easily and securely guided until engagement is reached.

The central body, in this case, has a length which allows the handle on the actuating end to be able to protrude sufficiently out of the housing of the exchangeable needle cartridge and to be comfortably actuated or rather rotated. Consequently, the drill chuck portion with the magnetic mounting is released from the screw connection of the one receiving portion which remains connected to the housing of the drive.

The exchangeable tool holds the drill chuck portion of the exchangeable docking device to be removed such that said drill chuck portion can be removed through the opening using the tool; a drill chuck portion which is then to be mounted is then placed onto the tool and inserted through the opening into the housing of the exchangeable needle cartridge. In this case, care is taken regarding the positioning and the drill chuck portion can be screw-connected onto the receiving portion or onto a cylindrical threaded portion which is provided on the receiving portion.

The exchangeable tool is then removed out of the housing; the telescopic tube is extended again, inserted into the housing again and fastened on the exchangeable docking device. The fastening can be effected by means of reinforced pressing-in in order to ensure that the axial position of the exchangeable tool corresponds to that determined for the mounting, i.e. the exchangeable tool is centered in the correct manner and abuts against the axial stop.

A special pressing cap which is matched to the opening geometry of the cartridge housing opening can also be used for this purpose.

Finally, the threaded ring of the telescopic tube mounting is screw-connected and the needle is inserted.

The mounting method can be carried out simply and quasi without tools, apart from what has been mentioned, such that repairs connected to the drilling needle can be carried out in minutes at any time during the measuring jobs even in the field.

Further embodiments as well as some of the advantages which are connected to these and further embodiments will become clear and more easily understandable as a result of the following detailed description. Supportive in this respect is also the reference to the figures in the description, in which.

The exchangeable needle cartridge as claimed in the invention is provided for use in a drilling measuring device.

Figure 3:
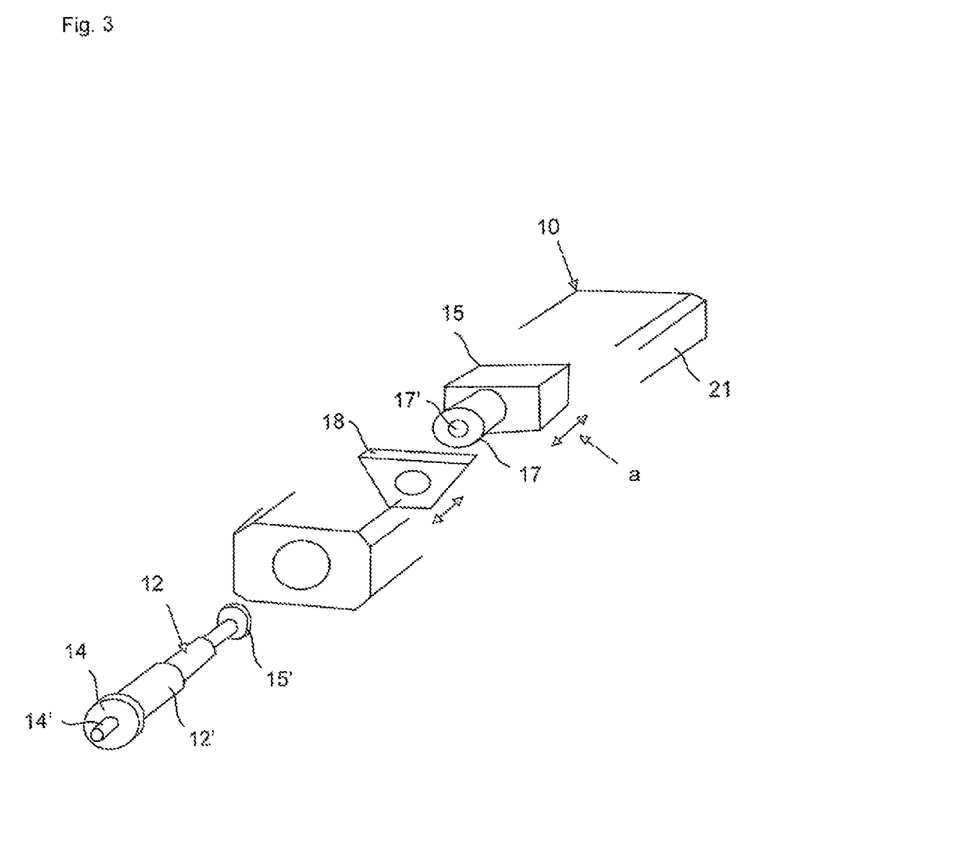
FIG. 3 shows a perspective exploded view of an exchangeable needle cartridge as claimed in one embodiment.

The exchangeable needle cartridge 10 as claimed in the invention, see FIG. 3, includes a telescopic tube 12 which is formed substantially by several telescopic tube portions 12'.

Figure 1:
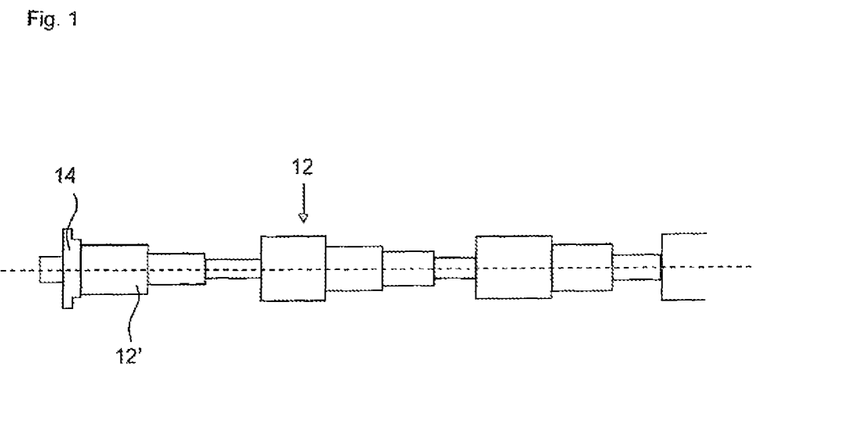
FIG. 1 shows a side view of a telescopic tube as claimed in an embodiment of the invention having the threaded ring mounting for the drilling needle.

As can be seen in FIG. 1, the telescopic tube 12 can be a quasi lengthened telescopic tube 12 which is composed of several telescopic tube sequences; in FIG. 1, in this case, the tube portion 12' with the largest diameter is always the one which faces the operating end of the telescopic tube 12, such a tube portion 12' consequently also receives the drilling needle (not shown) with the mounting 14 thereof. In principle, however, it is also possible to choose the arrangement with reference to the tube portion diameter in a reverse manner.

Figure 2:
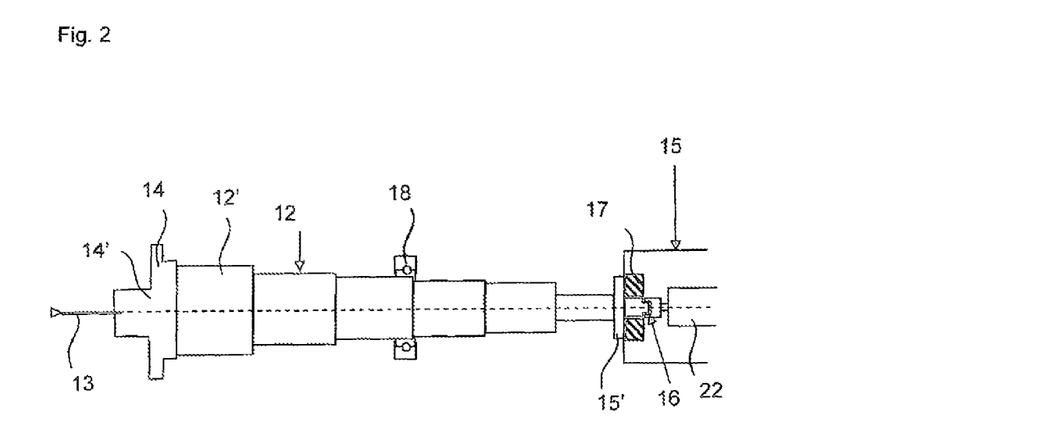
FIG. 2 shows a part side view-part sectional view of the telescopic tube of an embodiment of an exchangeable needle cartridge having the threaded ring mounting for the drilling needle, the supporting device, the magnetic mounting and the coupling.

As claimed in the invention, the drilling needle 13, see FIG. 2, is fastened in a non-rotatable manner on one operating end of the telescopic tube 12 by means of the mounting 14. The mounting 14, which is realized here as a threaded ring for screw-connection onto the operating end of the telescopic tube 12, has a corresponding drilling needle receiving means 14' for this purpose.

Figure 5:
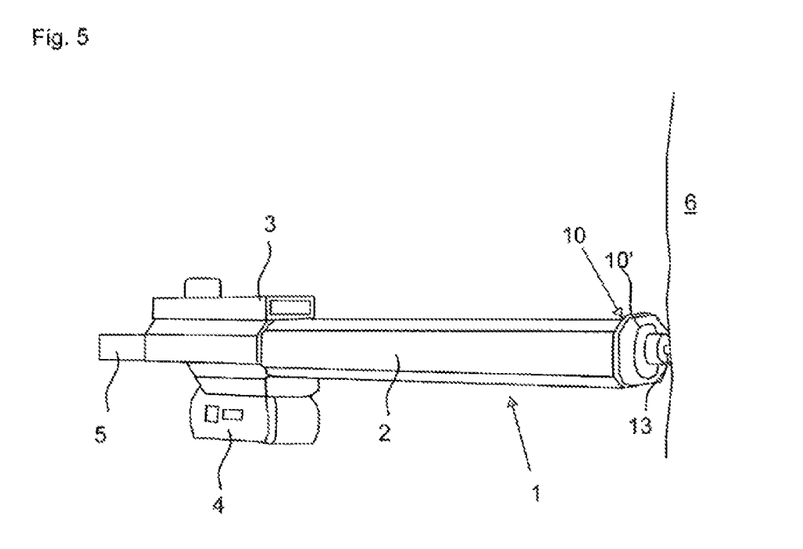
FIG. 5 shows a perspective side view of a drilling measuring device having an exchangeable needle cartridge.
Figure 6:
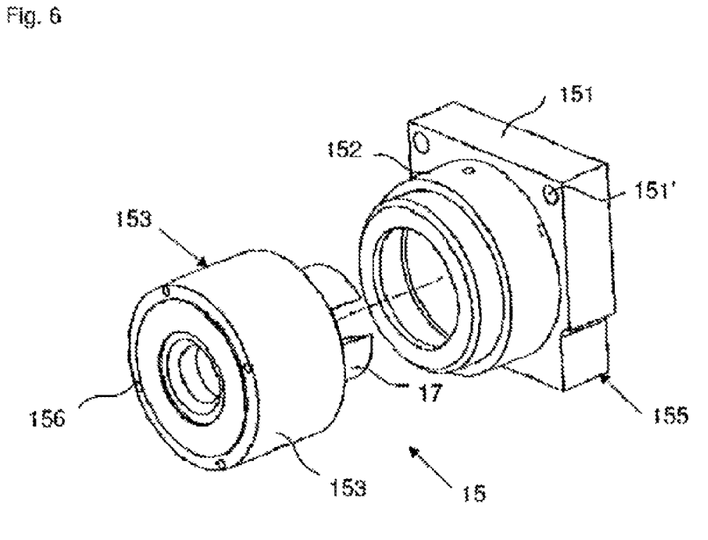
FIG. 6 shows a perspective side view of an exchangeable docking device in the non-connected state.
Figure 7:
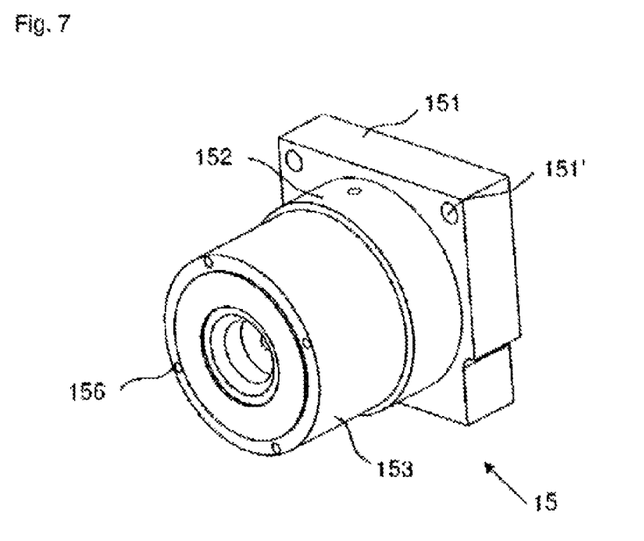
FIG. 7 shows a perspective side view of the exchangeable docking device from FIG. 6 in the connected state.

The variant in which the operating end with the mounting 14 for the drilling needle 13 is formed by a tube portion 12' with the largest diameter, whilst the tube portion 12' with the smallest diameter forms the docking end of the telescopic tube 12 on which the telescopic tube 12 is coupled to the docking device 15 is shown here in the figures and serves the purpose of operatively coupling the telescopic tube 12 and consequently the drilling needle 13 to a driving device of the drilling resistance measuring device 1, see FIG. 5.

The torque is transferred from the driving device of the drilling resistance measuring device 1 to the telescopic tube 12 by way of a coupling device 16 (also shown in FIG. 4) which is included by the docking device 15. So that the drilling needle 13, which is fastened on the operating end of the telescopic tube 12, is able to be inserted into an object 6, see FIG. 5, in order to measure the drilling resistance thereof or also the moving force, the telescopic tube 12 extends out from a telescoped initial position in order to drive the drilling needle 13 forward. The telescopic tube 12 carries out in a corresponding manner both a rotational movement and a linear movement. For the latter, the exchangeable needle cartridge 10 or the docking device 15 has a gear device in order to convert the rotational movement of the driving device of the drilling measuring device into a linear movement of the telescopic tube.

The docking device 15 has a magnetic mounting 17, to which the docking end of the telescopic tube 12 can be releasably connected such that the telescopic tube 12 with the drilling needle 13 is able to be easily exchanged. The magnetic mounting 17, in this case, as can be seen in FIGS. 2 and 3, is realized as a hollow cylinder, in the bore 17' of which the docking end of the telescopic tube 12 is received such that axial centering of the telescopic tube 12 is provided and the drilling needle 13 is aligned with a drive axis. The magnetic mounting 17 consequently functions as a type of drill chuck.

Figure 8:
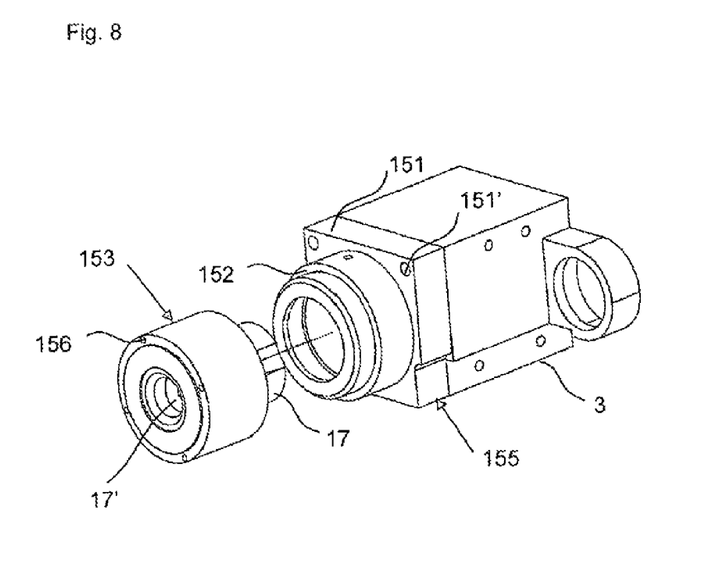
FIG. 8 shows a perspective side view of the exchangeable docking device from FIG. 6, arranged on a drive housing.
Figure 9:
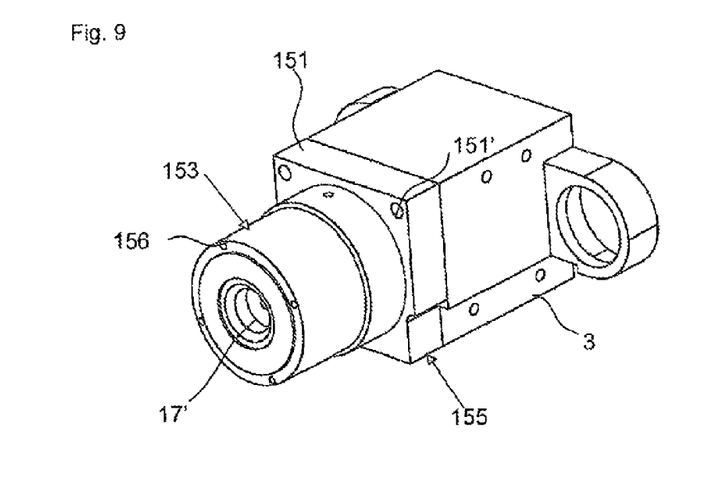
FIG. 9 shows a perspective side view of the exchangeable docking device from FIG. 6 in the connected state, arranged on a drive housing.
Figure 10:
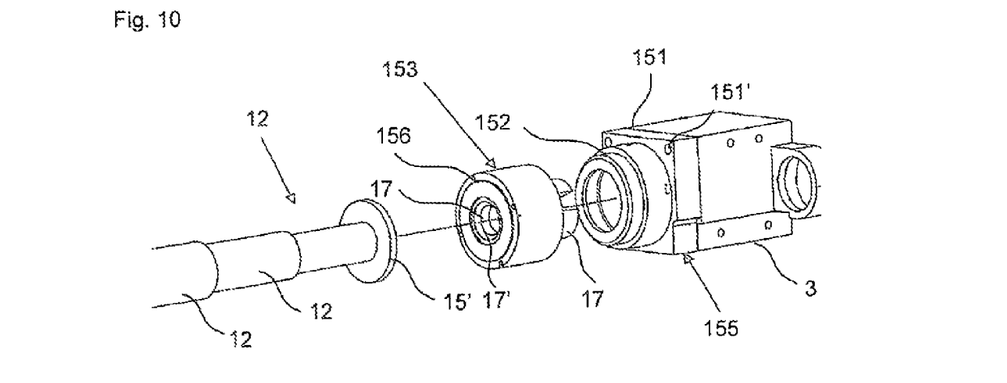
FIG. 10 shows a perspective side view of the exchangeable docking device from FIG. 6, in the non-connected state, with a telescopic tube located in the arrangement position.

The docking device 15 can be realized as an exchangeable docking device 15, as is shown in FIGS. 8 to 10: It then has a drill chuck portion 153 in which the described docking device is present with a magnetic mounting 17, and which can be connected to a receiving portion 155. This latter can be connected to the drilling measuring device, or to the drive housing 3 thereof. To this end, the receiving portion 155 can be provided with bores 151' by means of which a screw connection with the drive housing 3 is made.

Said portion remains arranged on the housing 3 of the motor or of the drive, whilst the drill chuck portion 153, shown in a separated manner in FIG. 8, is connectable to the cylindrical threaded portion 152 of the receiving section 155 by means of screw connection. The screw-connected arrangement is shown in FIG. 9.

FIG. 2 shows a docking device 15 in which the docking end of the telescopic tube 12 is mounted in a centered manner in the magnetic holder 17. The centered insertion of the docking end of the telescopic tube 23 into the magnetic mounting 17 is supported by the centering disc 15' which is arranged around the docking end of the telescopic tube 12 and abuts against the docking device 15 or the magnetic mounting 17 in the docked state. The docking end of the telescopic tube 12 is coupled here by means of a claw coupling 16 to a drive shaft 22 which is operatively connected to the driving device of the drilling resistance measuring device 1. Thus, the magnetic mounting 17 with the centering disc 15' facilitates the centered insertion of the docking end and consequently its coupling with the drive shaft 22. The docking end of the telescopic tube 12, in this case, has either a coupling piece which has positive locking elements or itself has the positive locking elements which form the claw coupling 16 with the corresponding counter positive locking elements on the drive side.

Apart from the previously described magnetic mounting with the claw coupling, other docking devices are also conceivable, for instance in the manner of a bayonet closure or a latching coupling. In the event of a bayonet closure, the individual telescopic tube segments should be connected together in order to enable rotation of the telescopic tube locking the bayonet closure.

The drill chuck portion 153 of the exchangeable docking device 15, just as the docking device 15 which is not provided for exchange, can also be operatively coupled with the telescopic tube 12 by means of its end remote from the receiving portion 155. The telescopic tube 12 which is already positioned for fastening can be seen in FIG. 10; the centering disc 15' points to the opening 17' of the magnetic mounting 17 which is present in the drill chuck portion 153.

On the end face of the drill chuck portion 153, in this case there are four openings 156 which, for the mounting or removal of the drill chuck portion 153 of the exchangeable docking device 15, are moved to engage with the dowel pins 205 which are present on the end face of the central portion 201 of the exchangeable tool 200.

For mounting or removal purposes, the exchangeable tool can be inserted into the housing 21 of the exchangeable needle cartridge 10 and placed onto the drill chuck portion 153 in order to enable the releasing of the drill chuck portion 153.

Figure 11:
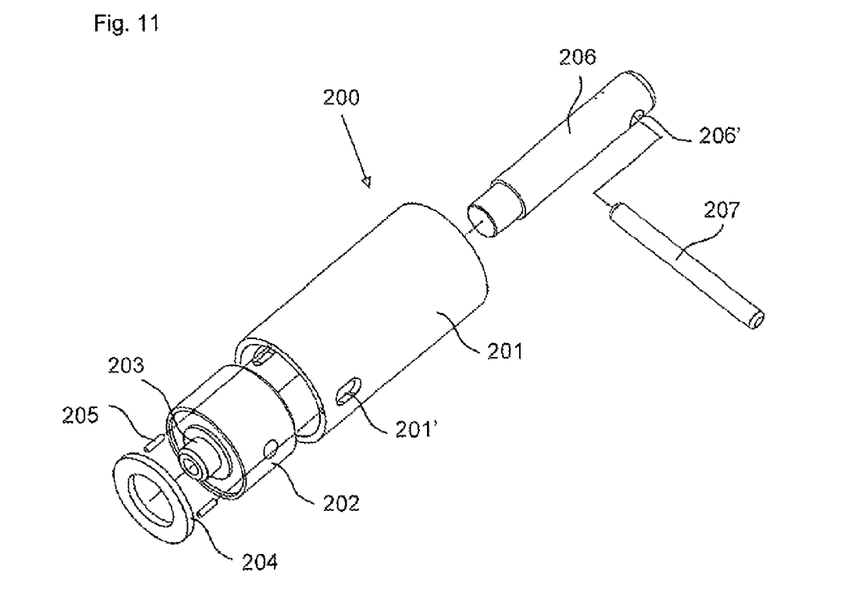
FIG. 11 shows an exploded view of a perspective side view of the exchangeable tool.
Figure 12:
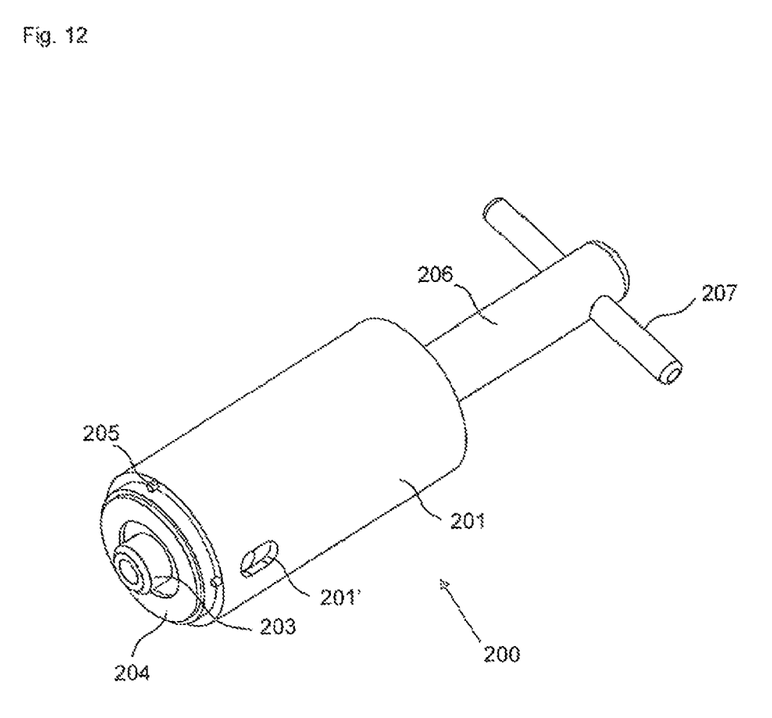
FIG. 12 shows a perspective side view of the exchangeable tool.

The embodiment of the tool 200 shown in FIGS. 11 and 12, through the use of the bearing cylinder 202, which supports the center-axially arranged cylindrical shaft portion 203 and its inner shaft 206 in order to hold the same on the end face of the engagement end of the tool 200, in this case has a centering projection, which is realized such that, when the exchangeable tool 200 is arranged for mounting/removal in the exchangeable needle cartridge 10, it is guidable in a precisely fitting manner over the step which is formed on the docking device 15 by the recess for the centering disc 15'.

Thus, the tool 200 forms a snug fit on the drill chuck portion 153 and, as a result of the interaction between the dowel pins 205 and the bores 156, is able to be rotated in order to release the drill chuck portion 153 from the receiving portion 155 in this way.

In addition, the central portion of the tool has two elongated holes 201' which extend in the axial direction, overlap the bores 202 on the bearing cylinder 202 and are able to receive fastening pins for fastening the bearing cylinder 202 in the central portion 201.

The fastening pins can be pressable radially outward by means of suitable measures, as a result of which the central portion 201 and the bearing cylinder 202 are advantageously lockable when mounted. In addition, a steel disc 204 abuts against the end face of the bearing cylinder 202, said steel disc being realized for the purpose of facilitating the insertion of the exchangeable tool 200 into the corresponding step in the drill chuck portion 153 as a result of the steel disc 204 being attracted by the magnetic field of the magnetic mounting 17.

As can be seen further, the handle, which is necessary to actuate the tool, is formed by the bar 207 which is arranged in the radial bore 206' of the bar 206 on the actuating end of the tool 200.

Figure 4:
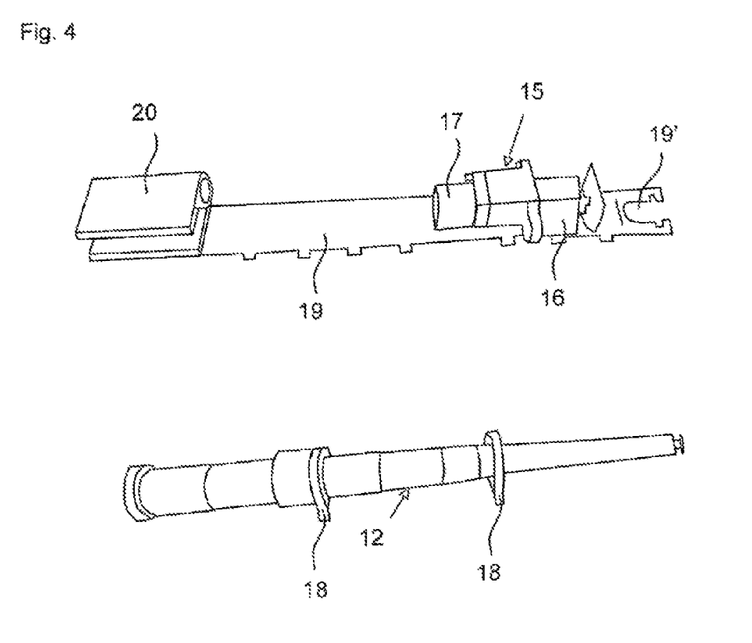
FIG. 4 shows a perspective top view of a telescopic tube and a rail with a docking device and guiding housing of an exchangeable needle cartridge as claimed in the invention.

So that the telescopic tube 12, which telescopes in operation, is guided, the exchangeable needle cartridge 10 includes at least one bearing 18 (FIGS. 2, 3, 4) which is arranged on one of the tube portions 12' between the operating end and the docking end. As can be seen in FIG. 4, two bearings 18 can also be provided on two different tube portions 12'.

A suitable gear device, in order to convert the rotational movement of the driving device into a linear movement for the telescopic tube 12, is, for instance, a spindle drive which is connected, for example, to the operating end of the telescopic tube 12 such that, as a result of said coupling, the telescopic tube 12 is able to be lengthened or shortened again after use.

As can be seen further in FIG. 4, the exchangeable needle cartridge 10 can include a rail 19, along which both the docking device 15 and a guiding housing 20 are arranged. The rail 19 also has a bifurcation 19' as the fastening means for releasably fastening the exchangeable needle cartridge 10 in the housing 2 of the drilling measuring device 1. The fastening is effected in the manner of a snap-lock or click-lock closure and does not require any expensive or time-consuming mounting or tools. The operating end of the telescopic tube 12 with the mounting 14 for the drilling needle 13 is received in the guiding housing 20 when it is extended.

In the variant shown in FIG. 4 (in the mounted state) in which the components 20, 25, 12 are arranged along a rail 19, the exchangeable needle cartridge 10 can be inserted into the housing 2 of the drilling measuring device 1.

The cartridge is even more elegantly manageable when, as indicated in FIG. 3 in the exploded view, the exchangeable needle cartridge 10 also has a housing 21, the bottom of which is formed by the rail 19. In an advantageous manner (see FIG. 5), the side of the guiding housing 20 which surrounds the operating end of the telescopic tube is realized there as a cartridge cover 10' which closes off with the edge of the front part of the multiple-part housing 2 of the drilling measuring device.

The drilling measuring device 1 with the exchangeable needle cartridge 10 as claimed in the invention and shown as an example in FIG. 5 additionally has a handle 5, by means of which it is held by a tester during measuring. The accumulator 4 is provided as an energy storage means for the drive which is housed in a first part of the housing 2; a display 3 with actuating means to display the measured values obtained and/or operating parameters for the drive is housed on the top surface of the first part of the housing 2.

The invention claimed is:

1. An exchangeable needle cartridge for a drilling measuring device, said exchangeable needle cartridge having a guiding device for a drilling needle, which guiding device is realized as a telescopic tube with a plurality of telescopic tube portions, wherein the plurality of telescopic tube portions extends between an operating end, on which a mounting is arranged for holding the drilling needle in a non-rotatable manner, and a docking end, on which a docking device of the exchangeable needle cartridge is arranged for coupling the telescopic tube with a driving device of the drilling measuring device, wherein the docking device comprises
  a coupling device for transmitting torque from the driving device of the drilling measuring device to the telescopic tube and
  a gear device for converting the rotational movement of the driving device of the drilling measuring device into a linear movement of the telescopic tube and
  means for detachably fastening the exchangeable needle cartridge on the drilling measuring device,
  wherein the needle together with the guiding device is able to be exchanged in toto from the driving device, wherein the docking device is an exchangeable docking device which has
  a drill chuck portion with a magnetic mounting and
  a receiving portion which is connectable to the drilling measuring device, wherein the drill chuck portion is releasably connectable at one end to the guiding device and at the other end to the receiving portion and the receiving portion has at least one fastening device which is realized for the purpose of fastening the receiving portion on the drilling measuring device.

2. The exchangeable needle cartridge as claimed in claim 1, wherein the drill chuck portion of the exchangeable docking device can be screw-connected to the receiving portion using a screw mechanism.

3. The exchangeable needle cartridge as claimed in claim 1, wherein the mounting is realized as a threaded ring and includes a drilling needle receiving means.

4. The exchangeable needle cartridge as claimed in claim 1, wherein the exchangeable needle cartridge includes at least one bearing for the telescopic tube, said bearing being arranged in a non-rotatable manner on a tube portion located between the operating end and the docking end, wherein the bearing is displaceable with the tube portion.

5. The exchangeable needle cartridge as claimed in claim 1, wherein the gear device includes a spindle drive which is connected to the operating end of the telescopic tube.

6. A drilling measuring device for testing material quality, said drilling measuring device including a driving device for driving a drilling needle, wherein the drilling measuring device has a housing in which the exchangeable needle cartridge as claimed in claim 1 is received at least in part in an operating arrangement of the drilling measuring device, wherein the drilling needle is coupled with the driving device using the telescopic tube and the docking device and wherein fastening means, which engage in a releasable manner with corresponding fastening means of the exchangeable needle cartridge, are arranged on the drilling measuring device housing.

7. The drilling measuring device as claimed in claim 6, wherein the drilling measuring device is a drilling resistance measuring device and/or a moving force measuring device, wherein the housing of the drilling measuring device is in multiple parts, wherein the exchangeable needle cartridge is received in a first part and the drive in a second part.

8. The drilling measuring device as claimed in claim 6, wherein the housing has at least a length and a geometry in such a manner that one or several bearings, which support the telescopic tube, are supported so as to be displaceable in the housing.

9. The drilling measuring device as claimed in claim 8, wherein the housing has at least a length and a geometry in such a manner that the exchangeable needle cartridge is received completely in the housing of the drilling measuring device.

10. The drilling device as claimed in claim 8, wherein the side of the guiding housing which surrounds the operating end of the telescopic tube is realized as a cartridge cover which closes off with an edge of the housing.

11. An exchangeable needle cartridge for a drilling measuring device, said exchangeable needle cartridge having a guiding device for a drilling needle, which guiding device is realized as a telescopic tube with a plurality of telescopic tube portions, wherein the plurality of telescopic tube portions extends between an operating end, on which a mounting is arranged for holding the drilling needle in a non-rotatable manner, and a docking end, on which a docking device of the exchangeable needle cartridge is arranged for coupling the telescopic tube with a driving device of the drilling measuring device, wherein the docking device comprises a coupling device for transmitting torque from the driving device of the drilling measuring device to the telescopic tube and a gear device for converting the rotational movement of the driving device of the drilling measuring device into a linear movement of the telescopic tube and means for detachably fastening the exchangeable needle cartridge on the drilling measuring device, wherein the needle together with the guiding device is able to be exchanged in toto from the driving device, wherein the docking device is an exchangeable docking device which has a drill chuck portion with a magnetic mounting and a receiving portion which is connectable to the drilling measuring device, wherein the drill chuck portion is releasably connectable at one end to the guiding device and at the other end to the receiving portion and the receiving portion has at least one fastening device which is realized for the purpose of fastening the receiving portion on the drilling measuring device, wherein on an end face of its end pointing away from the receiving portion, the drill chuck portion has engagement means, in particular at least two bores which are realized for the purpose of being moved into engagement with complementary engagement means of an exchangeable tool for the exchangeable docking device.

12. An exchangeable needle cartridge for a drilling measuring device, said exchangeable needle cartridge having a guiding device for a drilling needle, which guiding device is realized as a telescopic tube with a plurality of telescopic tube portions, wherein the plurality of telescopic tube portions extends between an operating end, on which a mounting is arranged for holding the drilling needle in a non-rotatable manner, and a docking end, on which a docking device of the exchangeable needle cartridge is arranged for coupling the telescopic tube with a driving device of the drilling measuring device, wherein the docking device comprises a coupling device for transmitting torque from the driving device of the drilling measuring device to the telescopic tube and a gear device for converting the rotational movement of the driving device of the drilling measuring device into a linear movement of the telescopic tube and means for detachably fastening the exchangeable needle cartridge on the drilling measuring device, wherein the needle together with the guiding device is able to be exchanged in toto from the driving device, wherein the docking or the exchangeable docking device includes a magnetic mounting which is releasably connected to the docking end of the telescopic tube and which provides an axial centering means for the docking end of the telescopic tube with the coupling device, wherein the coupling device provides in particular a claw coupling, a latching coupling or a bayonet closure.

13. The exchangeable needle cartridge as claimed in claim 12, wherein the magnetic mounting is a hollow cylinder, in the bore of which the docking end of the telescopic tube is received, and/or the docking end of the telescopic tube has a centering disc which abuts against the docking device, in particular against the magnetic mounting.

14. An exchangeable needle cartridge for a drilling measuring device, said exchangeable needle cartridge having a guiding device for a drilling needle, which guiding device is realized as a telescopic tube with a plurality of telescopic tube portions, wherein the plurality of telescopic tube portions extends between an operating end, on which a mounting is arranged for holding the drilling needle in a non-rotatable manner, and a docking end, on which a docking device of the exchangeable needle cartridge is arranged for coupling the telescopic tube with a driving device of the drilling measuring device, wherein the docking device comprises a coupling device for transmitting torque from the driving device of the drilling measuring device to the telescopic tube and a gear device for converting the rotational movement of the driving device of the drilling measuring device into a linear movement of the telescopic tube and means for detachably fastening the exchangeable needle cartridge on the drilling measuring device, wherein the needle together with the guiding device is able to be exchanged in toto from the driving device, wherein said exchangeable needle cartridge includes a rail along which the docking device is arranged, wherein the rail has the means for detachably fastening the exchangeable needle cartridge on the drilling measuring device, wherein the means for detachably fastening is a bifurcation.

15. The exchangeable needle cartridge as claimed in claim 14, wherein the rail forms one side of an exchangeable needle cartridge housing which can be inserted into a housing of the drilling resistance measuring device and can be received at least in part in the housing of the drilling resistance measuring device.

16. The exchangeable needle cartridge as claimed in claim 14, wherein the operating end of the telescopic tube is received in a guiding housing which is arranged along the rail on the end which is remote from the docking device.

17. The exchangeable needle cartridge as claimed in claim 16, wherein the side of the guiding housing which surrounds the operating end of the telescopic tube is realized as a cartridge cover which, when the exchangeable needle cartridge is arranged in the housing of the drilling resistance measuring device, is suitable to close off with an edge of the housing.

18. An exchangeable docking device, realized for the operative coupling of a guiding device for a drilling needle, said exchangeable docking device being operable with a drilling measuring device, wherein the guiding device is realized as a telescopic tube with a plurality of telescopic tube portions, wherein the exchangeable docking device has a drill chuck portion with a magnetic mounting and a receiving portion which is connectable to the drilling measuring device, wherein the drill chuck portion is releasably connectable at one end to the guiding device and at the other end to the receiving portion and the receiving portion has at least one fastening device which is realized for the purpose of fastening the receiving portion on the drilling measuring device.

19. The exchangeable docking device as claimed in claim 18, wherein the drill chuck portion is connectable to the receiving portion using a rotatable mechanism, and/or in that on an end face of its end pointing away from the receiving portion, the drill chuck portion has engagement means, in particular at least two bores which are realized for the purpose of being moved into engagement with complementary engagement means of an exchangeable tool for the exchangeable docking device.

20. An exchangeable tool for the exchanging of an exchangeable docking device as claimed in claim 18 or for the exchanging of an exchangeable docking device which is included in an exchangeable needle cartridge for a drilling measuring device, said exchangeable needle cartridge having a guiding device for a drilling needle, which guiding device is realized as a telescopic tube with a plurality of telescopic tube portions, wherein the plurality of telescopic tube portions extends between an operating end, on which a mounting is arranged for holding the drilling needle in a non-rotatable manner, and a docking end, on which a docking device is arranged for coupling the telescopic tube with a driving device of the drilling measuring device, wherein the docking device comprises a coupling device for transmitting torque from the driving device of the drilling measuring device to the telescopic tube and a gear device for converting the rotational movement of the driving device of the drilling measuring device into a linear movement of the telescopic tube and means for detachably fastening the exchangeable needle cartridge on the drilling measuring device, wherein the exchangeable tool has a central portion, the one end of which is realized as an engagement end for engagement with the exchangeable docking device, and which has on the end face a cylindrical shaft portion which is arranged in a center-axial manner and has an outer circumference which corresponds to the inner circumference of the bore of the hollow cylinder of the exchangeable docking device, and on said end face has on a at least two engagement means which are realized for engagement with the complementary engagement means which are present on the end face of the drill chuck portion of the exchangeable docking device, and the other end of which is realized as an actuating end and on which a handle is arranged.

21. The exchangeable tool as claimed in claim 20, wherein the at least two engagement means are dowel pins, and the complementary engagement means which are present on the end face of the drill chuck portion of the exchangeable docking device are bores, and in that an outer circumference of the central portion is smaller than or equal to a circumference of an opening which is present in the cartridge cover.

22. The exchangeable tool as claimed in claim 20, wherein the center-axially arranged cylindrical shaft portion extends center-axially through the central portion and projects out of said portion at the actuating end, and on its free end has a radial bore through which a bar protrudes and forms the handle, or in that the center-axially arranged cylindrical shaft portion is hollow and receives an inner shaft which extends center-axially through the central portion and projects out of said portion at the actuating end, and on its free end has a radial bore through which a bar protrudes and forms the handle.

23. The exchangeable tool as claimed in claim 20, wherein the center-axially arranged cylindrical shaft portion and/or the inner shaft on the end face of the engagement end are held by a bearing cylinder, wherein in particular the bearing cylinder is arranged in the central portion such that a centering projection is realized which, in the case of an arrangement of the exchangeable tool for mounting/removal in the exchangeable needle cartridge, is guidable in a precisely fitting manner over the step which is formed on the docking device by the recess for the centering disc.

* * * * *